(12) United States Patent
Nagashima et al.

(10) Patent No.: US 6,847,448 B2
(45) Date of Patent: Jan. 25, 2005

(54) POLARIZATION ANALYZING APPARATUS AND METHOD FOR POLARIZATION ANALYSIS (75) Inventors: Takeshi Nagashima, Suita (JP); Masanori Hangyo, Takatsuki (JP); Kouichi Hiranaka, Matsuyama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 280 days.

(21) Appl. No.: 10/180,193

(22) Filed: Jun. 26, 2002

(65) Prior Publication Data
US 2003/0016358 A1 Jan. 23, 2003

(30) Foreign Application Priority Data
Jun. 27, 2001 (JP) ......................................... 2001-195395

(51) Int. Cl.[7] .................................................. G01J 4/00
(52) U.S. Cl. ....................... 356/364; 356/365; 356/366; 356/369
(58) Field of Search ................................ 356/364, 365, 356/368, 369, 317, 318, 319, 320

(56) References Cited
U.S. PATENT DOCUMENTS
6,556,306 B2 * 4/2003 Jiang et al. ................. 356/517
6,661,519 B2 * 12/2003 Fukasawa ................... 356/432
2002/0067480 A1 * 6/2002 Takahashi ................... 356/317
2003/0165003 A1 * 9/2003 Ciesla et al. ................ 359/326

FOREIGN PATENT DOCUMENTS
JP           10142060 A      5/1998
JP        2001141567 A       5/2001
JP        2001151916 A       6/2001

* cited by examiner

*Primary Examiner*—Layla G. Lauchman
(74) *Attorney, Agent, or Firm*—Akin Gump Strauss Hauer & Feld, LLP (57) ABSTRACT A polarization analyzing apparatus includes: a light source for generating optical pulses; a light dividing part; an electromagnetic wave radiation part; a collimation part; a polarizer part; a light analyzer part; a condenser part; an optical time-delay part; an electromagnetic wave detector part; and a calculation part which Fourier-transforms time-resolved waveforms obtained by time-resolving electrical signals of s- and p-polarized electromagnetic waves reflected from a sample, and calculates amplitude and phase information of the s- and p-polarized electromagnetic waves.

8 Claims, 6 Drawing Sheets

PRIOR ART

FIG. 6

POLARIZATION ANALYZING APPARATUS AND METHOD FOR POLARIZATION ANALYSIS

BACKGROUND OF THE INVENTION

The present invention relates to an analyzing apparatus and an analyzing method for performing the measurement of optical and electrical characteristics of materials employing the spectroscopic method, and in particular, it relates to an analyzing apparatus and an analyzing method for material measurement in non-destructive and non-contacting way without necessitating the use of any reference.

Time-domain spectroscopic method in the terahertz-wave region (100 GHz to 20 THz) is a spectroscopic method having a feature of direct measurement capability for the complex optical constants such as complex refractive index comprised of refractive index and extinction coefficient of material in this frequency region, the complex electrical conductivity, or the complex dielectric constant without requiring the Kramers-Kronig transformation or the like. Furthermore, from the complex optical constants in the terahertz-wave region, various information on solid, liquid, or gas phase materials, which are difficult to obtain from measurement in other frequency ranges, can be obtained. Furthermore, non-destructive and non-contacting measurements of the complex optical constants are possible. From such background as mentioned above, research and development of time-domain spectroscopy in the terahertz-wave region and material research using it are pursued energetically.

While a lot of researches employing the terahertz time-domain spectroscopy have been implemented on solid, liquid and gas phase materials, many of them were conducted on the transmittance measurement of the terahertz electromagnetic wave. In some of other conventional researches, reflected electromagnetic wave from a sample was measured in order to derive the optical constant of the sample having a small terahertz electromagnetic wave transmittance.

Figure 5:
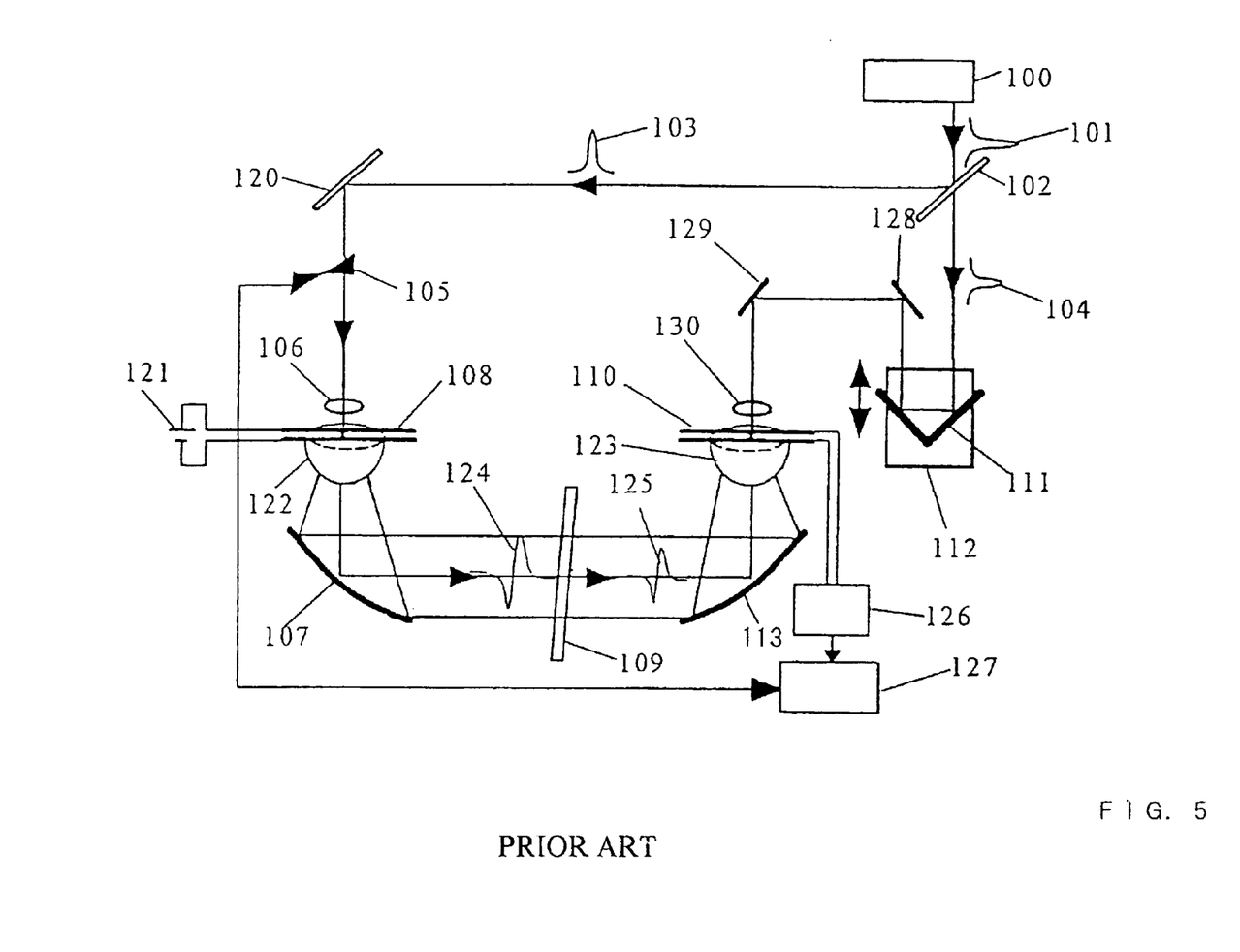
FIG. 5 is an outline configuration drawing of time-domain spectroscopic analyzing apparatus of a prior art 1.

Outline of the time-domain spectroscopy in accordance with a transmittance measurement of a prior art 1 is explained referring to FIG. 5. In the time-domain spectroscopy of the prior art 1, both of electromagnetic wave transmitting through a sample and electromagnetic wave without placing the sample (reference data) are measured.

FIG. 5 is an outline drawing of a time-domain spectroscopy of prior art 1. A pulse laser 100 generates an optical laser pulse 101. A beam splitter 102 divides input optical laser pulse 101 into optical laser pulses 103 and 104, and outputs them. The optical laser pulse 103 is used for radiating electromagnetic wave while the optical laser pulse 104 is used for triggering an electromagnetic wave detection photoconductive device 110. The optical laser pulse 103 is incident via a mirror 120, a chopper 105, and a lens 106 onto a radiation antenna 108 that is a terahertz electromagnetic wave radiation photoconductive device.

The radiation antenna 108 radiates terahertz electromagnetic wave 124 by inputting the optical laser pulse 103. The terahertz-wave 124 generated is collimated by a hemispherical lens 122 and a parabolic mirror 107 and is incident on a sample 109. A stabilized power supply 121 feeds electric power to the radiation antenna 108.

A chopper 105 is a rotating device having opened sector parts and closed sector parts alternatively, and it repeats transmission and interruption of the laser pulse 103 at a period of 1 to 3 kHz.

Terahertz electromagnetic wave 125 passing through the sample 109 is condensed by a parabolic mirror 113 and a hemispherical lens 123, and incident on a receiving antenna 110 that is a terahertz electromagnetic wave detection photoconductive device placed at a position symmetric to the position of the radiation antenna 108. The receiving antenna 110 that is a detecting device outputs a signal that is proportional to electric field of the teraheretz electromagnetic wave applied at an instant of excitation by femtosecond laser pulse 104.

The other laser pulse 104 divided at the beam splitter 102 is inputted to the receiving antenna 110 via a retro-reflector 111 forming a reflecting mirror, a mirrors 128, 129, and lens 130. By moving a movable stage 112 on which the retro-reflector 111 is fixed in the direction indicated by arrows, timing (amount of time-delay of illumination timing) at which the laser pulse 104 excites the receiving antenna 110 can be changed. A current amplifier 126 amplifies the output signal from the receiving antenna 110. A lock-in amplifier 127 inputs an output signal of the current amplifier 126 and a rotation control signal (or rotation detection signal) of the chopper 105, and then take out component corresponding to the rotation of chopper 105 from among the output signal of the current amplifier 126.

Figure 6:
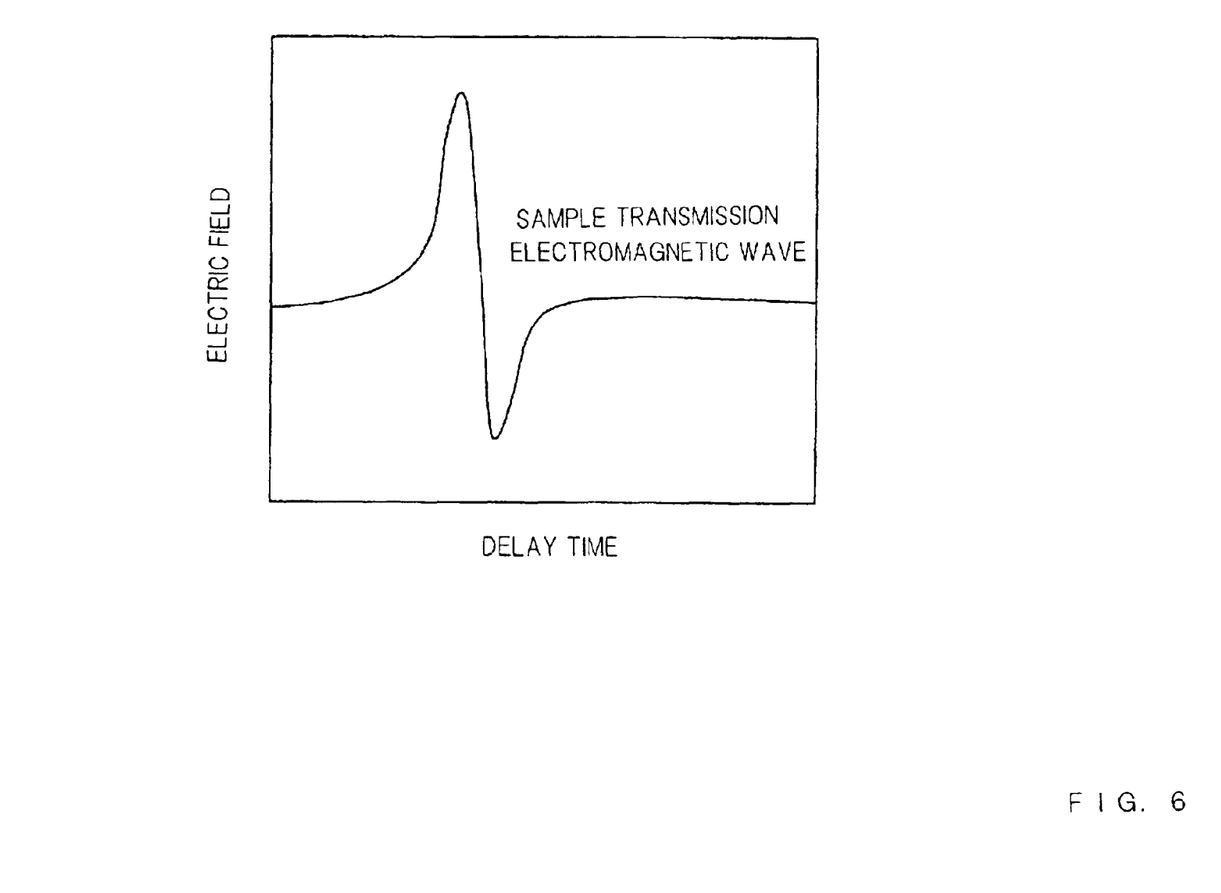
FIG. 6 is a conceptual graph of detected signal (time-resolved waveform) obtained by the time-domain spectroscopic analyzing apparatus of a prior art 1.

While changing the amount of time-delay by moving the movable stage 112, amplitudes of the output signal (electric field of terehertz electromagnetic wave) from the lock-in amplifier 127 at respective delay-time are measured. As a result, time-resolved waveform of radiated terehertz electromagnetic wave as shown in FIG. 6 (amplitude/amount of time-delay characteristics of electric field) can be measured.

As has been described above, the time-resolved waveforms themselves of terhertz electromagnetic wave, that is, amplitude/phase characteristics of electromagnetic wave can be measured. Measuring the time-resolved waveforms for the case of inserting the sample in the path of electromagnetic wave and for the case of not inserting it, respectively, then taking a ratio between complex spectra resulted respectively from respective Fourier transformations, the complex transmittance spectrum of the sample is obtained. Thereby, complex optical constants such as complex refractive index or the complex electric conductivity of the sample can be obtained all at once over a wide range of terahertz-wave region.

In the time-domain spectroscopy of a prior art 2, measuring a time-resolved waveform of electromagnetic wave reflected from the surface of a sample of the measuring objective and a time-resolved waveform of electromagnetic wave reflected from the surface of a material (reference) serving as the reference whose reflectance is known to be 1, and then taking a ratio between their complex spectra, the complex reflectance spectrum of the sample is obtained.

While in the prior art 1 the transmitted light through a sample is measured, in a prior art 2 the reflected light from a sample is measured. On the rest of the above point, they have the same configuration.

In the time-domain spectroscopy of the prior art 2 utilizing the reflected light, however, in order to know the phase information with an ample accuracy, it is necessary to make matching between the positions of the reflecting surfaces of a sample and a reference within an accuracy less than several micrometers (T. I. Jeon and D. Grischkowsky: Applied Physics Letters, Vol.72, 3032–3035 (1998)). This is very difficult to achieve with a mechanical accuracy of ordinary sample holders. In order to avoid this difficulty, a novel method is developed, in which, a transparent material of known film thickness and known refractive index onto the surface of the sample is attached, both of reflected electromagnetic wave at the surface of the transparent film and reflected electromagnetic wave at the interface between the transparent film and the sample are measured, and by performing data processing taking the film thickness and the refractive index of the transparent film into account, an enough accuracy is obtained (Shigeki Najima et al., 2001 (Heisei 13) 61st Applied Physics Autumn Academic Conference). However, this method has a problem that a certain processing step onto the sample is necessary and the data processing includes vexatious complexity.

In the time-domain spectroscopy utilizing the reflected light, trial of obtaining the optical constants without performing any measurement on a reference is also attempted. A method is proposed, in which, while changing the incident angle onto the sample, the Brewster angle is obtained by measuring the reflected waveform, and then from those data, the refractive index of a thin film on a substrate, that is a sample, is obtained (M. Li et al.: Applied Physics Letters, Vol. 74, 2113–2114 (1999)). Although this method is excellent in enabling the measurement of the optical constant of extremely thin film, it is necessary to move the position of a receiving antenna at each time when the incident angle is changed. In the time-domain spectroscopy, as it is necessary to adjust the light path of a femto-second pulse laser triggering the receiving antenna at each time when the incident angle is changed, it requires a vast time and effort in measurement, which makes the method unpractical. Moreover, by this proposed method, continuous spectrum cannot be obtained.

BRIEF SUMMARY OF THE INVENTION

In consideration of the above-mentioned problem, it is the purpose of the present invention to offer an apparatus and a method by which the complex optical constant spectra can be measured in high accuracy even on a sample of low electromagnetic wave transmittance in a reflection measurement at a single incident angle without any reference measurement and furthermore without applying any extra processing on a sample.

In order to achieve the above-mentioned purpose, the present invention has a configuration described below.

A polarization analyzing apparatus from an aspect of the present invention has: a light source for generating optical pulses; a light dividing part for dividing optical pulses emitted from the above-mentioned light source; an electromagnetic wave radiation part for inputting one of divided optical pulses and radiating electromagnetic wave; a collimation part for collimating the radiated electromagnetic wave; a polarizer part for inputting the collimated electromagnetic wave and letting polarized electromagnetic wave pass therethrough, and also capable of switching over its polarization plane; a light analyzer part for inputting the above-mentioned polarized electromagnetic wave reflected from a sample and letting the polarized electromagnetic wave component pass therethrough; a condenser part for condensing the above-mentioned passing polarized electromagnetic wave component; an optical time-delay part for variably causing a time-delay in the other divided optical pulses; and an electromagnetic wave detector part for inputting the above-mentioned condensed polarized electromagnetic wave component and the above-mentioned time-delayed other optical pulses, and converting the above-mentioned condensed polarized electromagnetic wave component into an electrical signal.

A polarization analyzing apparatus from other aspect of the present invention has: a light source for generating optical pulses; a light dividing device for dividing optical pulses emitted from the above-mentioned light source; an electromagnetic wave radiation device for inputting one of divided optical pulses and radiating electromagnetic wave; a first optical system for collimating the radiated electromagnetic wave; a polarizer for inputting the collimated electromagnetic wave and letting polarized electromagnetic wave pass therethrough, and also capable of switching over its polarization plane; a light analyzer for inputting the above-mentioned polarized electromagnetic wave reflected from a sample and letting the polarized electromagnetic wave component pass therethrough; a second optical system for condensing the above-mentioned passing polarized electromagnetic wave component; a third optical system for variably causing a time-delay in the other divided optical pulses; an electromagnetic wave detector for inputting the above-mentioned condensed polarized electromagnetic wave component and the above-mentioned time-delayed other optical pulses, and converting the above-mentioned condensed polarized electromagnetic wave component into an electrical signal.

The above-mentioned polarization analyzing apparatus from another aspect of the present invention has further: a calculation part for Fourier-transforming a time-resolved waveform obtained by time-resolving the above-mentioned electrical signal of s-polarized electromagnetic wave and p-polarized electromagnetic wave reflected from a sample, and calculating amplitude as well as phase information of s-polarized electromagnetic wave and p-polarized electromagnetic wave.

The Fourier transformation is a general numerical calculating process for extracting frequency components of a time-varying quantity.

The above-mentioned polarization analyzing apparatus from further another aspect of the present invention is characterized in that the above-mentioned calculation part further derives the complex optical constant spectra from amplitude and phase information of s-polarized electromagnetic wave and p-polarized electromagnetic wave reflected from a sample, using an amplitude reflectance ratio $r_p/r_s$ ($r_s$ and $r_p$ are respectively amplitude reflectance of s-polarized electromagnetic wave and p-polarized electromagnetic wave of a sample) and phase difference $\delta_p - \delta_s$ ($\delta_s$ and $\delta_p$ are respectively phases of s-polarized electromagnetic wave and p-polarized electromagnetic wave reflected from a sample).

The above-mentioned polarization analyzing apparatus from further another aspect of the present invention is characterized in that the frequency of the above-mentioned electromagnetic wave is in a frequency range from 100 GHz to 20 THz.

The above-mentioned polarization analyzing apparatus from further another aspect of the present invention is characterized in that the above-mentioned light source is a femto-second pulse laser or a semiconductor laser.

The above-mentioned polarization analyzing apparatus from further another aspect of the present invention is characterized in that the above-mentioned light dividing part or the above-mentioned light dividing device is a beam splitter.

A polarization analyzing method from further another aspect of the present invention has: a generating step of generating optical pulses from a light source; a dividing step of dividing the optical pulses emitted from the above-mentioned light source; an electromagnetic wave radiation step of inputting one of divided optical pulses and radiating electromagnetic wave; a collimation step of collimating the radiated electromagnetic wave; a first polarization step of extracting a first polarized electromagnetic wave from the collimated electromagnetic wave; a first detection step of detecting the above-mentioned first polarized electromagnetic wave reflected from a sample, using the other divided optical pulses; a second polarization step of extracting a second polarized electromagnetic wave from the collimated electromagnetic wave; a second detection step of detecting the above-mentioned second polarized electromagnetic wave reflected from a sample, using the above-mentioned other optical pulses; and an optical time-delay step of variably causing a time-delay in the above-mentioned other optical pulses.

The above-mentioned polarization analyzing method from further another aspect of the present invention is characterized in that the above-mentioned first polarized electromagnetic wave is one of s-polarized electromagnetic wave (electric field vector is perpendicular to the incidental plane) and p-polarized electromagnetic wave (electric field vector is parallel to the incidental plane), and the above-mentioned second polarized electromagnetic wave is the other one.

The present invention has a feature to be able to realize a polarization analyzing apparatus and a polarization analyzing method wherein the complex optical constant spectra can be measured in high accuracy even on a sample of low electromagnetic wave transmittance in a reflection measurement at a single constant incident angle without necessitating any reference measurement and furthermore without applying any extra processing on a sample.

The novel features of the invention will be hereinafter fully described and particularly pointed out in the appended claims, and the configuration and details of the invention, together with other objects and features thereof, will become better understood and appreciated by reference to the following detailed description when considered in conjunction with the accompanying drawings.

It will be understood that all or part of the drawings are purely diagrammatic for illustrative purposes and do not necessarily present faithful depictions of the actual relative sizes or positions of the illustrated elements.

DETAILED DESCRIPTION OF THE INVENTION

In the following the description is made associated with drawings on embodiment specifically showing the best mode of implementation of the present invention.

Embodiment

In the following a polarization analyzing apparatus and a polarization analyzing method of the present invention are specifically explained using an embodiment. Hereupon, the present invention is not to be interpreted as to be limited to the embodiment described below.

Figure 1:
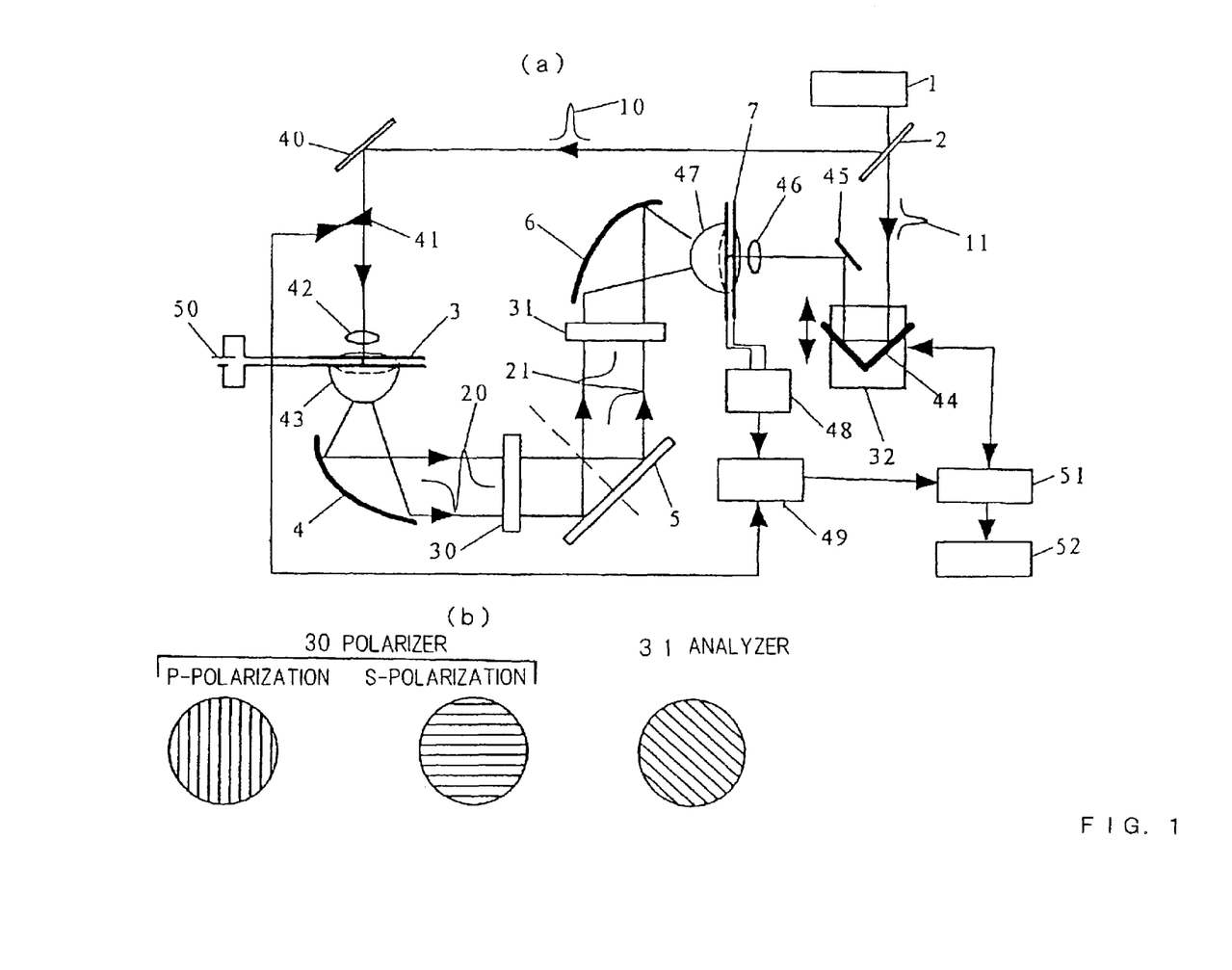
FIG. 1 shows an outline configuration drawing of an embodiment of the present invention.

FIG. 1(a) is an outlined configuration drawing of an embodiment of the present invention.

A pulse laser (light source) 1 generates optical laser pulses. As a light source a femto-second pulse laser or a semiconductor laser is used. The laser pulses are laser light of a wavelength of about 800 nm, pulse width of about 80 fs, and repetition frequency of about 80 MHz. A beam splitter 2 (light dividing part, light dividing device) divides input laser pulses and outputs optical laser pulses 10 and 11. The beam splitter 2 is a half mirror, for example. The optical laser pulse 10 is used for the electromagnetic radiation, while the optical pulse 11 is used as a trigger for a photoconductive antenna (receiving antenna) 7.

The optical laser pulse 10 is, via a mirror 40, a chopper 41, and a lens 42, incident onto a radiation antenna 3 that is a terahertz electromagnetic wave radiation photoconductive device (electromagnetic wave radiation part, electromagnetic wave radiation device). The radiation antenna 3 is comprised of a pair of conductive patterns drawn in parallel to each other (parallel electrodes) with an extremely narrow spacing on a plane perpendicular to the incident laser light(a plane perpendicular to the sheet plane of FIG. 1). By the illumination of the optical laser pulse 10, current flows instantaneously in the radiation antenna 3 (parallel electrodes). In the radiation antenna 3, transient current flows almost only in a time period while the optical laser pulse is projected onto the radiation antenna 3, and thereby the radiation antenna 3 radiates terahertz electromagnetic wave 20 (electromagnetic wave in the terahertz region (100 GHz to 20 THz)) having a pulse width from 50 fs to 10 ps. Generated electromagnetic wave is a linearly polarized wave having its magnetic component in a direction perpendicular to the current direction). The radiation antenna 3 used has a polarization dependent characteristic, and it is installed in such a way that the electric field vector having a maximum-valued electromagnetic wave at a time immediately after the illumination is in a plane perpendicular to the electromagnetic wave propagation direction and also forms an angle of 45 degrees with respect to the incident plane to a sample. Here, the incident plane to a sample means a plane including the propagation direction (direction of Poynting's vector) of the electromagnetic wave leaving from the radiation antenna 3, reflected at the sample, and arriving at the receiving antenna 7 (plane including the drawing sheet in FIG. 1(a).

A stabilized power supply 50 supplies electric power to the radiation antenna 3.

As a radiation antenna 3, any antenna can be used. For example, in place of the above-mentioned dipole antenna, a bow-tie antenna (radiating a linearly polarized wave) or a spiral antenna having a spiral-shaped electrode structure (radiating a circularly polarized wave) can be used. The terahertz electromagnetic wave radiated from a radiation antenna 3 is converted into a linearly polarized wave through the action of an polarizer and is incident on the sample.

A chopper 41 is a rotating device having opened sector parts and closed sector parts alternatively, and it repeats transmission and interruption of the laser pulse 10 at a period from 1 to 3 kHz.

Generated terahertz electromagnetic wave 20 is collimated by a hemispherical lens 43 and a parabolic mirror 4

(collimation part, first optics system) and is incident on a polarizer 30 (polarization part). The polarizer 30 lets particular polarized electromagnetic wave pass therthrough from among the terahertz electromagnetic wave 20. The polarizer 30 is a wire-grid formed with many metallic wires of the thickness of several micrometers arrayed keeping a space of about 10 micrometers. The polarizer 30 can be placed just in front of a sample 5 or just after the radiation antenna 3. It is preferable to set the polarizer 30 on a holder that makes a precise control of its azimuthal angle possible.

First, s-polarized electromagnetic wave (or p-polarized electromagnetic wave) is taken out from the terahertz electromagnetic wave 20 radiated from the radiation antenna 3 by the polarizer 30 (to let the electromagnetic wave pass through the polarizer 30). Under this situation, rotating the azimuthal angle of the polarizer 30 by an amount of 90 degrees, p-polarized electromagnetic wave (or s-polarized electromagnetic wave) can be taken out (Refer to FIG. 1(b)). The s-polarized electromagnetic wave is an electromagnetic wave whose electric field vector is perpendicular to its incident plane, while the p-polarized electromagnetic wave is an electromagnetic wave whose electric field vector is parallel to its incident plane.

If the radiation antenna 3 has no polarization-dependent characteristic, s-polarized electromagnetic wave and p-polarized electromagnetic wave which pass through the polarizer 30 have the same amplitude and the same phase. It may happen that the radiation antenna 3 has the polarization-dependent characteristic. In such a case, the radiation antenna 3 is installed in a way that the electric field vector having its maximum value at a position just after being radiated from the antenna 3 forms an angle of 45 degrees with respect to the incident plane. Thereby amplitudes and phases of s- and p-polarized electromagnetic waves become the same.

After the above-mentioned adjustment, s- and p-polarized electromagnetic waves are obliquely incident onto the sample keeping its collimation after adjusting the azimuthal angle of the polarizer.

Terahertz electromagnetic wave 21 reflected from the sample 5 (s-polarized electromagnetic wave or p-polarized electromagnetic wave) is incident on the analyzer 31 (analyzing part) keeping its collimation. The analyzer 31 is a wire grid of the same kind as that of the polarizer 30 (refer to FIG. 1(b)), which lets only the polarized component that gives the highest detection sensitivity for the receiving antenna 7 pass from among reflected electromagnetic waves. The terahertz electromagnetic wave 21 which passes through the analyzer 31 is condensed by a parabolic mirror 6 and a hemispherical lens 47 (condensation part, second optical system) and incident onto a receiving antenna 7 that is an electromagnetic wave detection photoconductive device (electromagnetic wave detecting part, electromagnetic wave detecting device). The receiving antenna 7 is comprised of a pair of conductive patterns drawn in parallel to each other with an extremely narrow spacing on a plane perpendicular to the electromagnetic wave propagation direction (a plane perpendicular to the sheet plane of FIG. 1). As a receiving antenna 7, any antenna capable of receiving a linearly polarized wave can be used. For example, in place of the above-mentioned dipole antenna, a bow-tie antenna can be used. The receiving antenna 7, which is a detecting device, outputs a signal that is proportional to the electric field of the terahertz electromagnetic wave applied at the moment of excitation by a femto-second laser pulse 11. The receiving antenna 7 transiently becomes conductive only while it is excited by the femto-second laser pulse 11, and after stopping this light illumination it returns to nonconductive. The receiving antenna 7 has a polarization-dependent characteristic, and it is installed so that its highest detection sensitivity direction is in a plane perpendicular to the electromagnetic wave propagation direction and forms an angle of 45 degrees with respect to the incident plane.

The optical laser pulse 11, which is the other laser pulse divided by the beam splitter 2 and is used for the electromagnetic wave detection, is incident on the receiving antenna 7 via a retro-reflector 44, which is a reflecting mirror, a mirror 45, and lens 46. When the optical laser pulse 11 is incident on the receiving antenna 7, the receiving antenna 7 shows the conductivity instantaneously. At this moment, current proportional to the electric field of the reflected electromagnetic wave 21 arriving at the receiving antenna 7 flows in the receiving antenna 7.

The retro-reflector 44 that is a reflecting mirror (optical time-delay part, third optical system) is placed between the beam splitter 2 and the receiving antenna 7. By moving the movable stage 32 on which the retro-reflector 44 is mounted in the direction indicated by arrows, the optical path length of the laser pulse 11 varies, and thus the timing at which the laser pulse 11 excites the receiving antenna 7 (amount of time delay (phase) of the illumination timing) varies. A current amplifier 48 amplifies the output signal of the receiving antenna 7. A lock-in amplifier 49 inputs an output signal of the current amplifier 48 and a rotation control signal (or rotation detecting signal), and thereby takes out a component corresponding to the rotation of the chopper 41 from among the output signal of the current amplifier 48.

As changing the amount of the time-delay by moving the movable stage 32, amplitudes of the output signal (electric field of the terahertz electromagnetic wave) of the lock-in amplifier 49 at respective delay-times are measured. As a result, time-resolved waveforms (time delay/amplitude characteristic) of radiated s-polarized electromagnetic wave and p-polarized electromagnetic wave are obtained.

Figure 2:
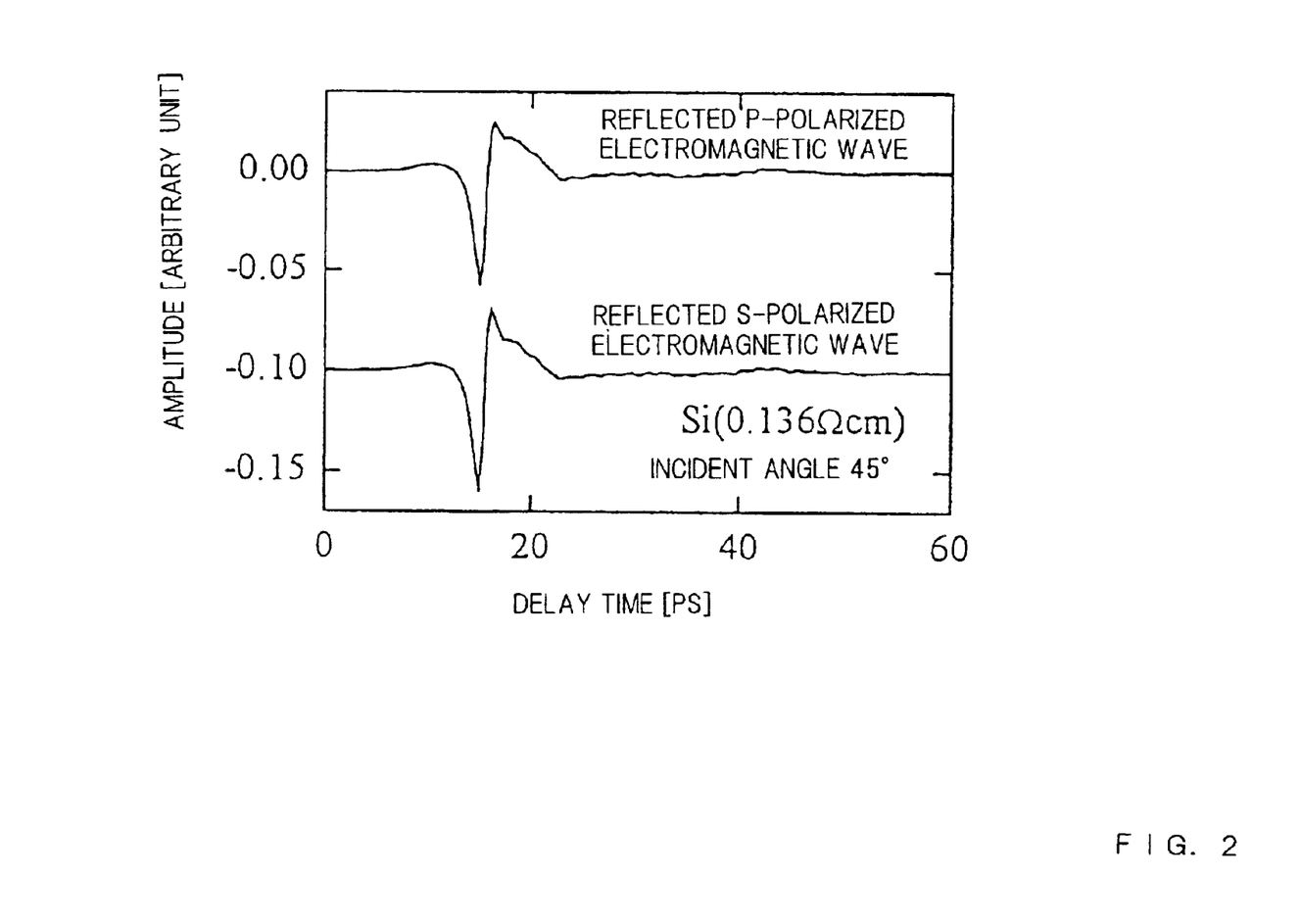
FIG. 2 shows a graph of a time-resolved waveform of reflected polarized electromagnetic wave concerning the present invention.
Figure 3:
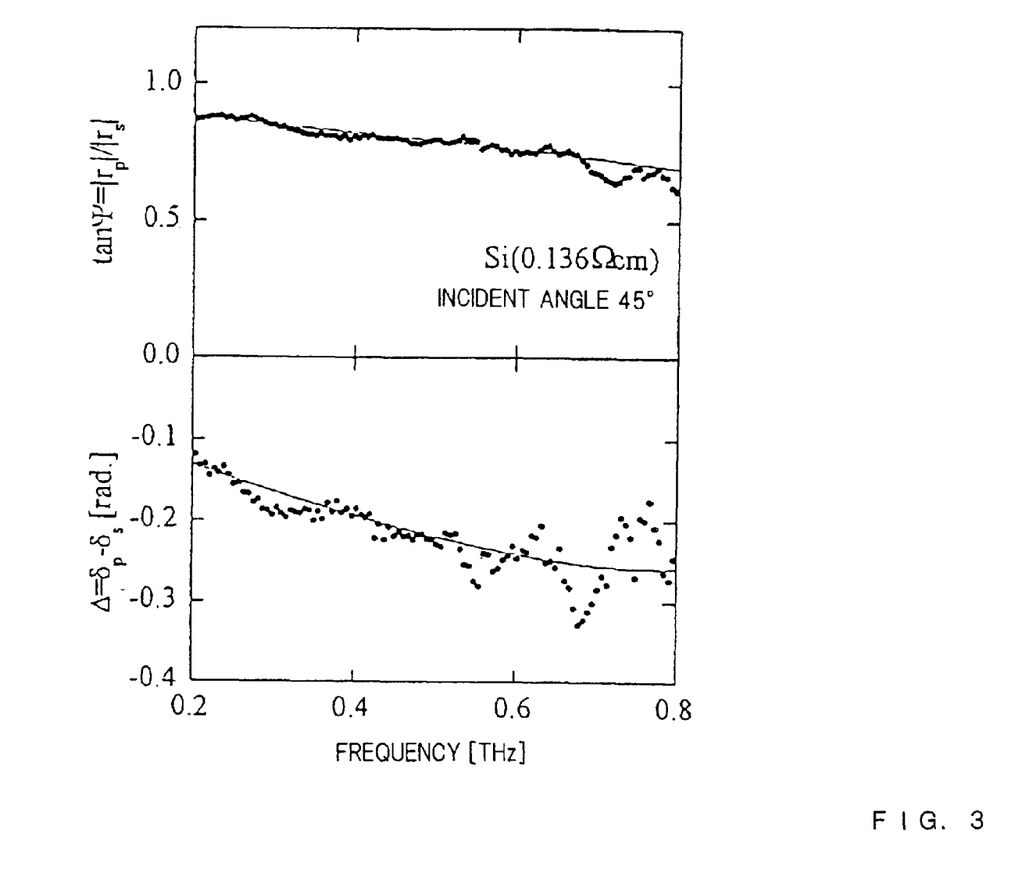
FIG. 3 shows a graph of frequency dependency of ellipsometric angles (amplitude reflectance and phase difference) calculated from data in FIG. 2.
Figure 4:
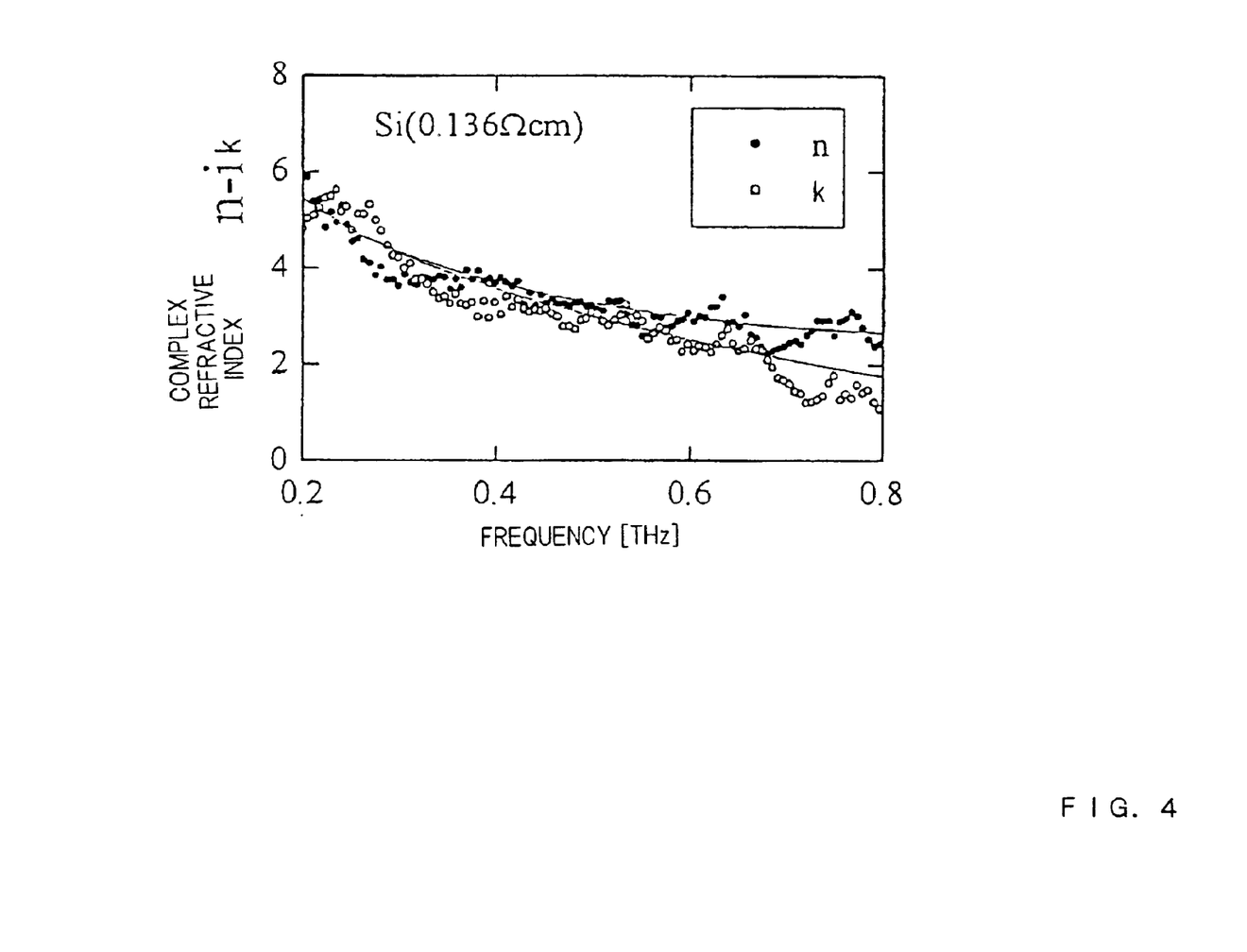
FIG. 4 shows plots of a complex refractive index calculated from data in FIG. 3.

Time-resolved waveforms $w_s(t)$ and $w_p(t)$ (t: time) of the reflected electromagnetic waves of s- and p-polarized electromagnetic waves from an n-type Si wafer (0.136 cm, 0.7 mm thickness) in case of incident angle of 45 degrees is shown in FIG. 2. And the ellipsometric angle variations depending on frequency obtained by taking a ratio between the respective Fourier transformations of those data shown in FIG. 2 are shown in FIG. 3. Complex refractive index spectra calculated from data of FIG. 3 are shown in FIG. 4. Hereupon, solid curves shown in FIG. 3 and FIG. 4 are calculated values by the Drude model.

In the polarization analyzing apparatus of the present embodiment, while a computer 51 is sending commands to move the movable stage 32 in a stepwise manner (while changing the timing at which the laser pulse 11 excites the receiving antenna 7), the output signals of the lock-in amplifier 49 (output signal of s-polarized electromagnetic wave and output signal of p-polarized electromagnetic wave) are inputted successively into the computer 51. After the output signal of the lock-in amplifier 49 (time-resolved waveform) is A/D-converted, data are stored in a memory of the computer 51.

In other embodiment, as a measurement operating personnel moves the movable stage 32 in a stepwise manner, he or she is reading out the output signal of the lock-in amplifier 49 successively, then inputting the read-out values into the computer 51.

AS for the wire grid of the polarizer 30, the directions through which the s-polarized electromagnetic wave and the p-polarized electromagnetic wave pass may be switched over by motorized way or by hand.

At the time of measurement, parts to be moved are only the azimuthal angle of the polarizer 30 and the position of the movable stage 32.

The collimation part, condenser part, and optical time-delay part are all constituted by optical means such as elliptical mirrors, lenses or the like.

The computer 51 (calculation processing part) computes the following calculations based on the above-mentioned measured data and displays calculated results as the objective parameters on a display 52.

By Fourier-transforming the time-resolved waveforms $w_s(t)$ and $w_p(t)$ (t: time) of the s- and p-polarized electromagnetic waves respectively, complex spectra $Es(v)$ and $Ep(v)$ containing amplitude and phase information of the reflected electromagnetic wave are obtained respectively. Here, $v$ is ($2\pi\times$ frequency).

$$Es(v) = |Es(v)|e^{i\delta_s(v)} \quad (1)$$

$$Ep(v) = |Ep(v)|e^{i\delta_p(v)} \quad (2)$$

By taking a ratio between complex spectra of s-polarized electromagnetic wave and p-polarized electromagnetic wave, spectra of the amplitude reflectance ratio between s-polarized electromagnetic wave and p-polarized electromagnetic wave $r_p(v)/r_s(v)$ and of the phase difference $\delta_p - \delta_s$ are obtained.

$$\frac{Ep(v)}{Es(v)} = \frac{|Ep(v)|}{|Es(v)|}e^{i\{\delta_p(v)-\delta_s(v)\}} = \frac{|r_p(v)|}{|r_s(v)|}e^{i\{\delta_p(v)-\delta_s(v)\}} \quad (3)$$

These are corresponding to respective terms of ellipsometric angles in polarization analyzing method that have been known heretofore, $\tan\Psi(v) \equiv r_p(v)/r_s(v)$ and $\Delta(v) \equiv \delta_p - \delta_s$. Then the complex optical constants spectra can be derived from the ellipsometric angles by the assistance of the polarization analyzing method. The method for obtaining the complex optical constant spectra from the obtained frequency dependent variation of the ellipsometric angle has been long and well known, and for example, it is described in a book of A. Azzam and N. M. Bashara, "Ellipsometry and Polarized Light" (North-Holland, 1987).

Letting the complex optical constant to be (n−ik) (n is a real part of complex optical constant, k is an imaginary part of complex optical constant), and the complex dielectric constant to be $\in = \in_1 - i \in_2$ ($\in_1$ is a real part of complex dielectric constant, $\in_2$ is an imaginary part of complex dielectric constant). Taking $\theta_0$ as the incident angle of electromagnetic wave onto a sample, $\in_1$ can be expressed by n and k as Eq.(4).

$$\varepsilon_1 = n^2 - k^2 = \sin^2\theta_0\left[1 + \frac{\tan^2\theta_0\{\cos^2(2\Psi) - \sin^2(2\Psi)\sin^2\Delta\}}{\{1+\sin(2\Psi)\cos\Delta\}^2}\right] \quad (4)$$

Similarly, $\in_2$ can be expressed by n and k as Eq.(5).

$$\varepsilon_2 = 2nk = \sin^2\theta_0\frac{\tan^2\theta_0\sin(4\Psi)\sin\Delta}{\{1+\sin(2\Psi)\cos\Delta\}^2} \quad (5)$$

Furthermore, these complex dielectric constants are in a relation with the complex electric conductivity $\sigma = \sigma_1 - i\sigma_2$ ($\sigma_1$ is a real part of electric conductivity, $\sigma_2$ is an imaginary part of electric conductivity) as expressed in Eq.(6) and Eq.(7), and electric characteristics can be measured by a method of non-contacting and non-destructive way without the necessity of forming of electrode pattern. Here, $\in_0$ is the vacuum dielectric constant.

$$\sigma_1 = \frac{v}{4\pi}\varepsilon_2 \quad (6)$$

$$\sigma_2 = \frac{v}{4\pi}(\varepsilon_0 - \varepsilon_1) \quad (7)$$

In accordance with the present invention, $\tan\Psi$ and $\Delta$, which are ellipsometric angles, can be obtained only by the measurement of time-resolved waveform of the reflecting wave of s-polarized electromagnetic wave and p-polarized electromagnetic wave at a single constant incident angle and any measurement of incident angle dependency is not required.

Furthermore, in accordance with the present invention, as has been described above, complex optical constant spectra of sample can be derived by the measurement of time-resolved waveforms of respective reflected electromagnetic waves under the states that the azimuthal angle of a polarizer is set to two mutually orthogonally crossing polarization directions.

In the conventional spectroscopic polarization analyzing method, since it was necessary to know the azimuthal angular dependency of the polarizer in detail, it was required to measure many times by changing the azimuthal angle little by little, but in the present invention the complex optical constant spectra can be obtained by a measurement of only two times.

The terahertz-wave polarization analyzing method and its apparatus of the present invention can derive various complex data by measuring the time-resolved waveform of a plural number of the polarized electromagnetic wave reflected from a sample. In the terahertz-wave polarization analyzing method and apparatus thereof, reference data are not measured.

As has been described above, the complex optical constant spectra of a sample can easily be obtained from the time-resolved waveform of the reflected wave of s-polarized and p-polarized electromagnetic wave without the necessity of measuring the reference such as a metallic mirror.

Furthermore, the sample is measurable if its region on which the electromagnetic wave is illuminated is flat, any particular extra process on it is not required. For example, by installing the present measuring apparatus into a thin film forming apparatus, on the spot observation of free carrier density and mobility of semiconductor or superconducting thin films, complex dielectric constant of ferroelectric materials, or organism (DNA, protein, enzyme or the like) becomes possible. For example, the rotational absorption lines of the molecule of the sample organism is detected by the present measuring apparatus, and the degree of extent of reaction is measured (or the existence of the specific DNA is detected).

In accordance with the present invention, an advantageous effect is obtained to be able to realize a polarization analyzing apparatus and a polarization analyzing method that make it possible to measure the complex optical constant spectra even of materials having low electromagnetic wave transmittance by a reflection measurement at a single constant incident angle without implementing any reference measurement, and furthermore without applying any extra processing on a sample.

Although the invention has been described in some detail dealing with the preferred embodiments, the configuration details of any of the preferred embodiments disclosed herein may be changed or modified, and any changes in the combination or order of elements thereof can be accomplished without departing from the spirit and scope of the invention as set forth in the appended claims.

What is claimed is:

1. A polarization analyzing apparatus characterized in having:
   a light source for generating optical pulses;
   a light dividing part for dividing optical pulses emitted from said light source;
   an electromagnetic wave radiation part for inputting one of divided optical pulses and radiating an electromagnetic wave;
   a collimation part for collimating the radiated electromagnetic wave;
   a polarizer part for inputting the collimated electromagnetic wave and letting a polarized electromagnetic wave pass therethrough, and also capable of switching over its polarization plane;
   a light analyzer part for inputting said polarized electromagnetic wave inflected from a sample and letting the reflected polarized electromagnetic wave component pass therethrough;
   a condenser part for condensing said passing polarized electromagnetic wave component;
   an optical time-delay part for variably causing a time-delay in the other divided optical pulses;
   an electromagnetic wave detector part for inputting said condensed polarized electromagnetic wave component and said time-delayed other optical pulses, and converting said condensed polarized electromagnetic wave component into an electrical signal; and
   a calculation part which Fourier-transforms time-resolved waveforms obtained by time-resolving said electrical signals of s- and p-polarized electromagnetic waves reflected from the sample, and calculates amplitude and phase information of the s- and p-polarized electromagnetic waves.

2. A polarization analyzing apparatus characterized in having:
   a light source for generating optical pulses;
   a light dividing device for dividing optical pulses emitted from said light source;
   an electromagnetic wave radiation device for inputting one of divided optical pulses and radiating an electromagnetic wave;
   a first optical system far collimating the radiated electromagnetic wave;
   a polarizer for inputting the collimated electromagnetic wave and letting a polarized electromagnetic wave pass therethrough, and also capable of switching over its polarization plane;
   a light analyzer for inputting said polarized electromagnetic wave reflected from a sample and letting its polarized electromagnetic wave component pass therethrough;
   a second optical system for condensing said passing polarized electromagnetic wave component;
   a third optical system for variably causing a time-delay in the other divided optical pulse;
   an electromagnetic wave detector for inputting said condensed polarized electromagnetic wave component and said time-delayed other optical pulses, and converting said condensed polarized electromagnetic wave component into an electrical signal; and
   a computer which Fourier-transforms time-resolved waveforms obtained by time resolving said electrical signals of s- and p-polarized electromagnetic waves reflected from the sample, and calculates amplitude and phase information of the s- and p-polarized electromagnetic waves.

3. The polarization analyzing apparatus as described in claim 1, characterized in that said calculation part further derives complex optical constant spectra from the amplitude and phase information of the s-polarized electromagnetic wave and the p-polarized electromagnetic wave reflected from the sample, using an amplitude reflectance ratio $r_p/r_s$ ($r_s$ and $r_p$ are respectively amplitude reflectance for the s-polarized electromagnetic wave and p-polarized electromagnetic wave of a the sample) and a phase difference $\delta_p - \delta_R$ ($\delta_S$ and $\delta_p$ are respectively phases of the s-polarized electromagnetic wave and the p-polarized electromagnetic wave reflected from the sample).

4. The polarization analyzing apparatus described in claim 1, characterized in that the frequency of said electromagnetic wave is in a frequency range from 100 GHz to 20 THz.

5. The polarization analyzing apparatus described in claim 1, characterized in that said light source is a femtosecond pulse laser or a semiconductor laser.

6. The polarization analyzing apparatus described in claim 1, characterized in that said light dividing part or said light dividing device is a beam splitter.

7. A polarization analyzing method characterized in having:
   a generating step of generating optical pulses from a light source;
   a dividing step of dividing the optical pulses emitted from said light source;
   an electromagnetic wave radiation step of inputting one of divided optical pulses and radiating an electromagnetic wave;
   a collimation step of collimating the radiated electromagnetic wave;
   a first polarization step of extracting a first polarized electromagnetic wave from the collimated electromagnetic wave;
   a first detection step of detecting said first polarized electromagnetic wave reflected form a sample, using the other divided optical pulses;
   a second polarization step of extracting a second polarized electromagnetic wave from the collimated electromagnetic wave;
   a second detection step of detecting said second polarized electromagnetic wave reflected from the sample, using said other optical pulses;
   an optical time-delay step of variably causing a time-delay in said other optical pulses and
   a calculation step of Fourier-transforming time-resolve waveforms obtained by time-resolving electrical signals of s- and p-polarized electromagnetic waves (electric field vectors perpendicular and parallel to an incidental plane, respectively) reflected from the sample, said electrical signals derived at said first and second detection steps, and calculating amplitude and phase information of the s- and p-polarized electromagnetic waves.

8. The polarization analyzing method as described in claim 7, characterized in that said first polarized electromagnetic wave is one of the s- and p-polarized electromagnetic waves, and said second polarized electromagnetic wave is the other one.

* * * * *